United States Patent
Liu et al.

(10) Patent No.: US 7,342,137 B1
(45) Date of Patent: Mar. 11, 2008

(54) **CYCLOHEXENONE COMPOUNDS FROM *ANTRODIA CAMPHORATA* AND APPLICATION THEREOF**

(75) Inventors: Sheng-Yun Liu, Taipei Hsien (TW); Wu-Che Wen, Taipei Hsien (TW); Wan-Ling Tsou, Taipei Hsien (TW); Mao-Tien Kuo, Taipei Hsien (TW); Chun-Hung Huang, Taipei Hsien (TW); Ka-Hang Fok, Taipei Hsien (TW); Ya-Ying Li, Taipei Hsien (TW); Chun-Chou Chang, Taipei Hsien (TW)

(73) Assignee: Golden Biotechnology Corporation, Taipei Hsien (TW)

( * ) Notice: Subject to any disclaimer, the term of this patent is extended or adjusted under 35 U.S.C. 154(b) by 0 days.

(21) Appl. No.: 11/747,407

(22) Filed: May 11, 2007

(30) Foreign Application Priority Data

Jan. 8, 2007 (TW) .............................. 96100680 A

(51) Int. Cl.
*C07C 49/543* (2006.01)
*C07C 49/557* (2006.01)
*A61K 31/12* (2006.01)

(52) U.S. Cl. ........................................ 568/377; 514/690
(58) Field of Classification Search ..................... None
See application file for complete search history.

(56) References Cited

OTHER PUBLICATIONS

I-Hwa Cherng et al., Three New Triterpenoids from Antrodia Cinnamomea, Journal, Mar. 1995, vol. 58 No. 3, pp. 365-371, Journal of Natural Products.
Chung-Hsiung Chen et al., New Steroid Acids from Antrodia Cinnamomea a Fungal Parasite of Cinnamomum Micranthum, Journal, Nov. 1995, vol. 58 No. 11, pp. 1655-1661, Journal of Natural Products.
Hung-Chen Chiang et al., A sesquiterpene lactone, phenyl compounds from Antrodia cinnamomea, Journal, Jun. 1995, vol. 29 No. 2, pp. 613-616, Elsevier Science Ltd.
Shu-Wei Yang et al., Steriods and triterpenoids of Antodia cinnamomea-a fungus parasitic on Cinnamomum micranthus, Journal, Mar. 1996, vol. 41 No. 5, pp. 1389-1392, Elsevier Science Ltd.
I-Hwa Cherng et al., Triterpenoids form Antrodia cinnamomea, Journal, Jan. 1996, vol. 41 No. 1, pp. 263-267, Elsevier Science Ltd.

*Primary Examiner*—Sikarl A. Witherspoon
(74) *Attorney, Agent, or Firm*—WPAT, P.C.; Anthony King

(57) ABSTRACT

The present invention relates to a novel compound and its uses, which is an extract isolated and purified from Antrodia camphorate, in particular to 4-hydroxy-2,3-dimethoxy-6-methyl-5(3,7,11-trimethyl-dodeca-2,6,10-trienyl)-cyclohex-2-enone, and its use in tumor growth inhibition. The compound of the invention, which has never been discovered in Antrodia camphorate, can be applied in inhibiting the growth of cancer cells, such as breast cancer, hepatic cancer and prostate cancer; and be used as a pharmaceutical composition to inhibit the tumor growth; or further be applied in prevention of heart and blood vessel disease or dietary supplements for health needs through its antioxidant activity.

30 Claims, No Drawings

CYCLOHEXENONE COMPOUNDS FROM *ANTRODIA CAMPHORATA* AND APPLICATION THEREOF

BACKGROUND OF THE INVENTION

1. Field of the Invention

The present invention relates to a novel compound, in particular to an extract isolated and purified from Antrodia camphorata, and its use in inhibiting tumor growth.

2. The Prior Arts

Antrodia camphorata (Niu Chang-Zhi) is also called "Chang-Zhi", "Niu Chang-Ku", "Red-Chang", "Red Chang-Chih", "Chang-Ku", camphor chamber mushroom and so on, which is an endemic species in Taiwan growing on the inner rotten heart wood wall of Cinnamomum kanehirae Hay in the altitude of 450M to 2000M in the mountains of Taiwan. The fruit bodies of Antrodia camphorata grow inside of the tree trunk. Cinnamoum kanehirai Hay is distributed mainly in the mountain areas of Tao-Yuan, Nan-Tou and has been put on the rare and valuable list due to rare amount and over cutting unlawfully. The Antrodia camphorata in the wild thus became even rare. Because the growth rate of natural Antrodia camphorata is extremely slow, and its growth season is from June to October, therefore the price of Antrodia camphorata is very expensive.

The fruiting bodies of Antrodia camphorata are perennial, sessile, suberin or woody, with various appearances such as plate-like, bell-like, hoof-like, or tower-like shapes. They are flat on the surface of wood at the beginning of growth. Then the brim of the front edge arise to roll into plate-shaped or stalactites. The top surfaces of Antrodia camphorata are lustrous, brown to dark brown in color, with unobvious wrinkles, flat and blunt edges. The bottom sides are orange red or partially yellow with ostioles all over.

In addition, Antrodia camphorata exhales strong smell of sassafras (camphor aroma), becomes pale yellowish brown after sun-dried and has a strong bitter taste. In traditional Taiwanese medicine, Antrodia camphorata is commonly used for detoxification, liver protective, anti-cancer. Antrodia camphorate, like general edible and medicinal mushrooms, is rich in numerous nutrients including polysaccharides (such as β-glucosan), triterpenoids, superoxide dismutase (SOD), adenosine, proteins (immunoglobulins), vitamins (such as vitamin B, nicotinic acid), trace elements (such as calcium, phosphorus and germanium and so on), nucleic acid, agglutinin, amino acids, steroids, lignins and blood pressure stabilizers (such as antodia acid) and the like. These bioactive ingredients are believed to exhibit beneficial effects such as: anti-tumor, immunity enhancement, anti-allergy, inhibition of platelet agglutination, anti-virus, anti-bacteria, anti-hypertension, blood glucose-lowering, cholesterol-lowering, hepatic protection and the like.

Triterpenoids are the most studied component among the numerous compositions of Antrodia camphorate. Triterpenoids are the summary terms for natural compounds, which contain 30 carbon atoms with the pentacyclic or hexacyclic structures. The bitter taste of Antrodia camphorata is from the component of triterpenoids. Three novel ergostane-type triterpenoids (antcin A, antcin B, antcin C) were isolated by Cherng et al. from the fruiting bodies of Antrodia camphorata (Cherng, I. H., and Chiang, H. C. 1995. Three new triterpenoids from Antrodia cinnamomea. J. Nat. Prod. 58:365-371). Three new compounds named zhankuic acid A, zhankuic acid B and zhankuic acid were extracted from the fruiting bodies of Antrodia camphorata with ethanol by Chen et al. (Chen, C. H., and Yang, S. W. 1995. New steroid acids from Antrodia cinnamomea, a fungus parasitic on Cinnamomum micranthum. J. Nat. Prod. 58:1655-1661). In addition, Cherng et al. also found three other new triterpenoids from the fruiting bodies of Antrodia camphorate, which are sesquiterpene lactone and 2 biphenyl derived compounds, 4,7-dimethoxy-5-methyl-1,3-benzodioxole and 2,2',5,5'-teramethoxy-3,4,3',4'-bi-methylenedioxy-6,6'-dimethylbiphenyl (Chiang, H. C., Wu, D. P., Cherng, I. W., and Ueng, C. H.1995. A sesquiterpene lactone, phenyl and biphenyl compounds from Antrodia cinnamomea. Phytochemistry. 39:613-616). In 1996, four novel ergostane-type triterpenoids (antcins E and F and methyl antcinates G and H) were isolated by Cherng et al. with the same analytic methods (Cherng, I. H., Wu, D. P., and Chiang, H. C. 1996. Triteroenoids from Antrodia cinnamomea. Phytochemistry. 41:263-267). And two ergostane related steroids, zhankuic acids D and E together with three lanosta related triterpenes, 15 alpha-acetyl-dehydrosulphurenic acid, dehydroeburicoic acid, dehydrosulphurenic acid were isolated by Yang et al. (Yang, S. W., Shen, Y. C., and Chen, C. H.1996. Steroids and triterpenoids of Antrodia cinnamomea a fungus parasitic on Cinnamomum micranthum. Phytochemistry. 41:1389-1392). Searches for exact active ingredients in antitumor effect are still in the experimental stage, and are remained to be elucidated, though the antitumor effects of Antrodia camphorata extracts were reported (such as the abovementioned references). This will greatly contributes great beneficial effects on cancer treatment if the exact antitumor composition is found.

SUMMARY OF THE INVENTION

In order to identify the anti-tumor compounds from the extracts of Antrodia camphorate, the compound of the formula (1) was isolated and purified in this invention,

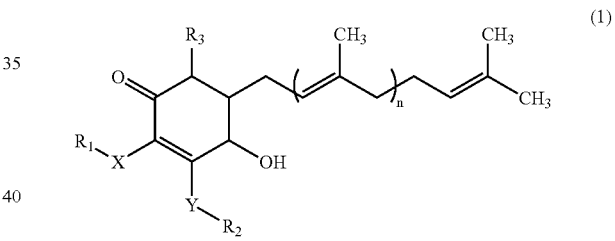

wherein X and Y can be oxygen or sulfur, $R_1$, $R_2$ and $R_3$ are each a hydrogen atom, methyl or $(CH_2)_m$—$CH_3$ and m=1-12; n=1-12.

A preferred compound of the general formula (1) is 4-hydroxy-2,3-dimethoxy-6-methyl-5(3,7,11-trimethyl-dodeca-2,6,10-trienyl)-cyclohex-2-enone as shown in formula (2), with molecular formula of $C_{24}H_{38}O_4$, appearance of pale yellow powder and molecular weight of 390.

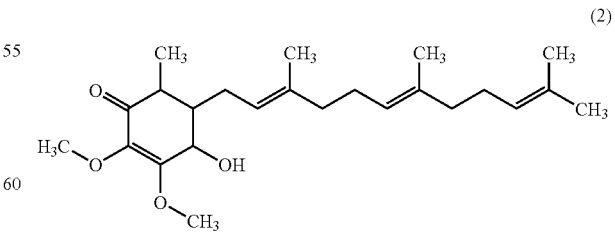

Compounds having the structures of formula (1) and formula (2) are purified from aqueous extraction or organic solvent extraction of Antrodia camphorata. The organic solvents used include, but not limited to, alcohols such as methanol, ethanol or propanol, esters such as ethyl acetate, alkanes such as hexane, or alkyl halides such as chloromethane, chloroethane. Among them, alcohol is preferred, and ethanol is particularly preferred.

With the compounds which can be used according to the invention, the growth of tumor cells can be inhibited, which can further be used as a medicinal composition to treat cancer and to enhance the therapeutic effects. The compounds of the invention can be applied in a range of cancer cells, including breast cancer, hepatic cancer and prostate cancer, which result in slowering the growth of cancer cells, further inhibiting proliferation of cancer cells and decreasing the risk of malignancy. Therefore they can be used in cancer treatment such as breast cancer, hepatic cancer, prostate cancer and the like.

On the other hand, the compounds of formula (1) and/or formula (2) in the invention can be incorporated into the medicinal compositions for treating breast cancer, hepatic cancer, and prostate cancer to inhibit the growth of tumor cells. The medicinal compositions include not only the compounds of formula (1) and/or formula (2), but also the pharmaceutically accepted carries. The carriers include, but are not limited to, excipients such as water, fillers such as sucrose or starch, binders such as cellulose derivatives, diluents, disintegrants, absorption enhancers or sweeteners. The pharmaceutical composition of the present invention can be manufactured through mixing the compounds of formula (1) and/or formula (2) with at least one of the carriers by means of conventional methods known in the pharmaceutically technical field, which can be formulated, but are not limited to, as a powder, tablet, capsule, pellets, granules or other liquid formulation.

In addition, because the compounds of the present invention possess antioxidant activity at the same time, they can be ideal supplements for health foods, diets and drinks, medical products and cosmetics and are beneficial to human health through their abilities in preventing cardiovascular diseases or mutation of cells.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

The mycelia, fruiting bodies or mixture of both from Antrodia camphorata are first extracted with water or organic solvents to obtain the aqueous extract or organic solvent extract of Antrodia camphorata using the methods well known in the arts. The organic solvents include, but not limited to, alcohols such as methanol; ethanol or propanol; esters such as ethyl acetate; alkanes such as hexane; or alkyl halides such as chloromethane, and chloroethane. Among them, alcohol is preferred, and ethanol is particularly preferred.

The aqueous or organic solvents extracts of Antrodia camphorate were subjected to high-performance liquid chromatography (HPLC) for isolation and purification. Each fraction was recovered and assayed for anti-cancer effects. The potent fractions with anti-cancer effects were analyzed for the composition and further assayed against different tumor cells. The above approach then led to the identification of novel compounds, the formula (1) and formula (2), which inhibited the growth of several tumor cells, had not been found in Antrodia camphorata and were not reported in any previous publication.

The compound 4-hydroxy-2,3-dimethoxy-6-methyl-5(3, 7,11-trimethyl-dodeca-2,6,10-trienyl)-cyclohex-2-enone of the formula (2) are explained below as an example for the present invention. The anti-cancer effects of the 4-hydroxy-2,3-dimethoxy-6-methyl-5(3,7,11-trimethyl-dodeca-2,6,10-trienyl)-cyclohex-2-enone was assessed by 3-(4,5-dimethylthiazol-2-yl)-2, S-diphenyl tetrazolium bromide (MTT) assay according to the anti-tumor drugs screening model of National Cancer Institute (NCI) on cell survival rates using cell lines such as breast cancer, hepatic cancer, prostate cancer and the like. The above assays had proved that 4-hydroxy-2,3-dimethoxy-6-methyl-5(3,7,11-trimethyl-dodeca-2,6,10-trienyl)-cyclohex-2-enone decreased survival rates of breast cancer cell lines (MCF-7 and MDA-MB-231), hepatocellular carcinoma cell lines (Hep 3B and Hep G2) and prostate cancer cell lines (LNCaP and DU-145), at the same time showed relatively low half inhibition concentration (IC50) values. The cancer cell growth of breast cancer, hepatic cancer, and prostate cancer was inhibited by 4-hydroxy-2,3-dimethoxy-6-methyl-5(3,7,11-trimethyl-dodeca-2,6,10-trienyl)-cyclohex-2-enone and which therefore can be used for cancer treatment such as breast cancer, hepatic cancer, prostate cancer and the like. The details of the examples are described as follows:

Example 1

Isolation of 4-hydroxy-2,3-dimethoxy-6-methyl-5(3, 7,11-trimethyl-dodeca-2,6,10-trienyl)-cyclohex-2-enone 100 g of mycelia, fruiting bodies or mixture of both from Antrodia camphorata were placed into a flask. A proper amount of water and alcohol (70-100% alcohol solution) was added into the flask and were stirred at 20-25° C. for at least 1 hour. The solution was filtered through a filter and 0.45 μm membrane and the filtrate was collected as the extract.

The filtrate of Antrodia camphorata was subjected to High Performance Liquid chromatography (HPLC) analysis. The separation was performed on a RP18 column, the mobile phase consisted of methanol (A) and 0.1-0.5% acetic acid (B), with the gradient conditions of 0-10 min in 95%~20% B, 10-20 min in 20%~10% B, 20-35 min in 10%~10% B, 35-40 min in 10%~95% B, at the flow rate of 1 ml/min. The column effluent was monitored with a UV-visible detector.

The fractions collected at 25-30 min were collected and concentrated to yield 4-hydroxy-2,3-dimethoxy-6-methyl-5 (3,7,11-trimethyl-dodeca-2,6,10-trienyl)-cyclohex-2-enone, a product of pale yellow powder. The analysis of 4-hydroxy-2,3-dimethoxy-6-methyl-5(3,7,11-trimethyl-dodeca-2,6,10-trienyl)-cyclohex-2-enone showed the molecular formula of $C_{24}H_{38}O_4$, molecular weight of 390, melting point of 48° C.~52° C. Investigation of NMR spectra showed that $^1$H-NMR (CDCl$_3$) δ (ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ (ppm)=12.31, 16.1, 16.12, 17.67, 25.67, 26.44, 26.74, 27.00, 39.71, 39.81, 4.027, 43.34, 59.22, 60.59, 120.97, 123.84, 124.30, 131.32, 135.35, 135.92, 138.05, 160.45, and 197.12.

The chemical structure of 4-hydroxy-2,3-dimethoxy-6-methyl-5(3,7,11-trimethyl-dodeca-2,6,10-trienyl)-cyclohex-2-enone was compared against the chemical compounds database and no similar structure was available. These data confirmed that 4-hydroxy-2,3-dimethoxy-6-methyl-5(3,7,11-trimethyl-dodeca-2,6,10-trienyl)-cyclohex-2-enone is a novel compound which has never been reported previously.

Example 2

In Vitro Survival Assay for Anti-Breast Cancer Effects

The NCI anti-cancer drug screen model was adopted to test the anti-cancer effect of the compound from example 1 in the invention. The isolated compound of 4-hydroxy-2,3-dimethoxy-6-methyl-5(3,7,11-trimethyl-dodeca-2,6,10-trienyl)-cyclohex-2-enone from example 1 was added into the culture media of human breast-cancer cells, MCF-7 or MDA-MB-231, for tumor cell survival assay. This assay can be tested with 3-[4,5-dimethylthiazol-2-yl]2,5-diphenyltetrazolium bromide (MTT) assay, which is commonly used to determine cell proliferation, percent of viable cells, and cytotoxicity. MTT is a yellow dye, which can be absorbed by the living cells and be reduced to purplish blue formazan crystals by succinate tetrazolium reductase in mitochondria. Formazan formation can therefore be used to assess and determine the survival rate of cells.

The human breast-cancer cells, MCF-7 and MDA-MB-231 were separately cultivated in media containing fetal calf serum for 24 hours. The proliferated cells were washed once with PBS, then treated with 1× trypsin-EDTA and centrifuged at 1200 rpm for 5 minutes. The supernatant was discarded and the cell pellet was resuspended in 10 ml of fresh culture medium by gently shaking. The cells were placed in a 96-well plate. Ethanol extracts of Antrodia camphorata (the control group, total extracts of Antrodia camphorata without purification) were added into each of the 96 wells at the following concentrations: 30, 10, 3, 1, 0.3, 0.1 and 0.03 μg/ml, respectively, while 4-hydroxy-2,3-dimethoxy-6-methyl-5(3,7,11-trimethyl-dodeca-2,6,10-trienyl)-cyclohex-2-enone (the experiment group) were added into each of the 96 wells at the following concentrations: 30, 10, 3, 1, 0.3, 0.1 and 0.03 μg/ml, respectively. The cells were incubated at 37° C. in a 5% $CO_2$ incubator for 48 hours. MTT was added in a concentration of 2.5 mg/ml into each well in dark and incubated for 4 hours, followed by the addition of 100 μl of lysis buffer to stop the reaction. The plates were read on an ELISA reader at wavelength of 570 nm to determine the survival rates. The half inhibition concentration ($IC_{50}$) values were also calculated and listed in Table 1.

TABLE 1

Results of in vitro survival assay for inhibition of breast cancer cells

| Samples | $IC_{50}$ (μg/ml) |
| --- | --- |
| Control group (extract of Antrodia camphorata) | |
| MCF-7 | 11.132 |
| MDA-MB-231 | 25.812 |
| Experiment group (formula 2) | |
| MCF-7 | 0.852 |
| MDA-MB-231 | 1.031 |

From the result of table 1, 4-hydroxy-2,3-dimethoxy-6-methyl-5(3,7,11-trimethyl-dodeca-2,6,10-trienyl)-cyclohex-2-enone is a potent inhibitor of the growth of human breast cancer cell line. The $IC_{50}$ values of 4-hydroxy-2,3-dimethoxy-6-methyl-5(3,7,11-trimethyl-dodeca-2,6,10-trienyl)-cyclohex-2-enone toward MCF-7 and MDA-MB-231 are 0.852 μg/ml and 1.031 μg/ml respectively, which are significantly lower than those of total extracts from Antrodia camphorate. Therefore 4-hydroxy-2,3-dimethoxy-6-methyl-5(3,7,11-trimethyl-dodeca-2,6,10-trienyl)-cyclohex-2-enone from Antrodia camphorata can be applied to inhibit the growth of breast cancer cells.

Example 3

In Vitro Add-on Study Toward Adjuvant Therapy of Breast Cancer Cells

The experiment was also carried out according to NCI anti-cancer drug screen in vitro model. The human breast-cancer cells, MCF-7 and MDA-MB-231 were separately cultivated in media containing fetal calf serum for 24 hours. The proliferated cells were washed once with PBS, then treated with 1× trypsin-EDTA and centrifuged at 1200 rpm for 5 minutes. The supernatant was discarded and the cell pellet was resuspended in 10 ml of fresh culture medium by gently shaking. The cells were placed in a 96-well plate after 0.0017 μg/ml Taxol was added and treated for 72 hours. 4-hydroxy-2,3-dimethoxy-6-methyl-5(3,7,11-trimethyl-dodeca-2,6,10-trienyl)-cyclohex-2-enone obtained from example 1 were added respectively into each of the 96 wells at the following concentrations: 0 μg/ml (the control group); 30, 10, 3, 1, 0.3, 0.1 and 0.03 μg/ml (the experiment group). The cells were incubated at 37° C. in a 5% $CO_2$ incubator for 48 hours. MTT was added in a concentration of 2.5 mg/ml into each well in dark and reacted for 4 hours, followed by the addition of 100 μl of lysis buffer to terminate the reaction. The plates were read on an ELISA reader at wavelength of 570 nm to determine the survival rates. The half inhibition concentration ($IC_{50}$) values were also calculated and listed in Table 2.

TABLE 2

Results from in vitro Taxol add-on therapy toward breast cancer cells

| Samples | Results |
| --- | --- |
| Control group | Cell survival rate (%) |
| MCF-7 (0.0017 μg/ml Taxol) | 65 ± 1 |
| MDA-MB-231 (0.0017 μg/ml Taxol) | 76 ± 3 |
| Experiment group | $IC_{50}$ (μg/ml) |
| MCF-7 (0.0017 μg/ml Taxol + formula 2) | 0.009 |
| MDA-MB-231 (0.0017 μg/ml Taxol + formula 2) | 0.011 |

From the result of table 2, the $IC_{50}$ values of 4-hydroxy-2,3-dimethoxy-6-methyl-5(3,7,11-trimethyl-dodeca-2,6,10-trienyl)-cyclohex-2-enone toward MCF-7 and MDA-MB-231 decreased to 0.009 μg/ml and 0.011 μg/ml respectively after addition of Taxol. Therefore these results confirm the inhibitory activity of 4-hydroxy-2,3-dimethoxy-6-methyl-5(3,7,11-trimethyl-dodeca-2,6,10-trienyl)-cyclohex-2-enone from Antrodia camphorata can be applied to inhibit the growth of breast cancer cells, and showed better antitumor synergistic activity for tumors when combined with Taxol.

Example 4

In Vitro Survival Assay for Anti-Hepatic Cancer Effects

The NCI anti-cancer drug screen model was also adopted to test the anti-cancer effect of the compound isolated from example 1 in the present invention. The isolated compound of 4-hydroxy-2,3-dimethoxy-6-methyl-5(3,7,11-trimethyldodeca-2,6,10-trienyl)-cyclohex-2-enone from example 1 was added into the culture media of human hepatic-cancer cells, Hep 3B or Hep G2, for tumor cell survival assay.

The human hepatic-cancer cells, Hep 3B and Hep G2, were separately cultivated in media containing fetal calf serum for 24 hours. The proliferated cells were washed once with PBS, then treated with 1× trypsin-EDTA and centrifuged at 1200 rpm for 5 minutes. The supernatant was discarded and the cell pellet was resuspended in 10 ml of fresh culture medium by gently shaking. The cells were placed in a 96-well plate. Ethanol extracts of Antrodia camphorata (the control group, total extracts of Antrodia camphorata without purification) were added into each of the 96 wells at the following concentrations: 30, 10, 3, 1, 0.3, 0.1 and 0.03 µg/ml, respectively, while 4-hydroxy-2,3-dimethoxy-6-methyl-5(3,7,11-trimethyl-dodeca-2,6,10-trienyl)-cyclohex-2-enone (the experiment group) were added into each of the 96 wells at the following concentrations: 30, 10, 3, 1, 0.3, 0.1 and 0.03 µg/ml, respectively. The cells were incubated at 37° C. in a 5% $CO_2$ incubator for 48 hours. MTT was added in a concentration of 2.5 mg/ml into each well in dark and incubated for 4 hours, followed by the addition of 100 µl of lysis buffer to stop the reaction. The plates were read on an ELISA reader at wavelength of 570 nm to determine the survival rates. The half inhibition concentration ($IC_{50}$) values were also calculated and listed in Table 3.

TABLE 3

Results of in vitro survival assay for inhibition of hepatic cancer cells

| Samples | $IC_{50}$ (µg/ml) |
|---|---|
| Control group | |
| (total extracts of *Antrodia camphorata*) | |
| Hep 3B | 5.121 |
| Hep G2 | 18.631 |
| Experiment group | |
| (formula 2) | |
| Hep 3B | 0.005 |
| Hep G2 | 1.679 |

From the result of table 3, 4-hydroxy-2,3-dimethoxy-6-methyl-5(3,7,11-trimethyl-dodeca-2,6,10-trienyl)-cyclohex-2-enone is a potent inhibitor of the growth of human hepatic cancer cell line. The $IC_{50}$ values of 4-hydroxy-2,3-dimethoxy-6-methyl-5(3,7,11-trimethyl-dodeca-2,6,10-trienyl)-cyclohex-2-enone toward Hep 3B and Hep G2 are 0.005 µg/ml and 1.679 µg/ml respectively, which are significantly lower than those of total extracts from Antrodia camphorata. Therefore 4-hydroxy-2,3-dimethoxy-6-methyl-5(3,7,11-trimethyl-dodeca-2,6,10-trienyl)-cyclohex-2-enone from Antrodia camphorata can be applied to inhibit the growth of hepatic cancer cells.

Example 5

In Vitro Add-on Study Toward Adjuvant Therapy of Hepatic Cancer Cells

The experiment was also carried out according to NCI anti-cancer drug screen in vitro model. The human hepatic cancer cells, Hep 3B and Hep G2 and MDA-MB-231 were separately cultivated in media containing fetal calf serum for 24 hours. The proliferated cells were washed once with PBS, then treated with 1× trypsin-EDTA and centrifuged at 1200 rpm for 5 minutes. The supernatant was discarded and the cell pellet was resuspended in 10 ml of fresh culture medium by gently shaking. The Hep 3B cells were treated with 0.0043 µg/ml of Lovastatin for 72 hours and Hep G2 cells were treated with 0.0017 µg/ml of Taxol for 72 hours before placing in a 96-well plate. 4-hydroxy-2,3-dimethoxy-6-methyl-5(3,7,11-trimethyl-dodeca-2,6,10-trienyl)-cyclohex-2-enone obtained from example 1 were added respectively into each of the 96 wells at the following concentrations: 0 µg/ml (the control group); 30, 10, 3, 1, 0.3, 0.1 and 0.03 µg/ml (the experiment group). The cells were incubated at 37° C. in a 5% $CO_2$ incubator for 48 hours. MTT was added in a concentration of 2.5 mg/ml into each well in dark and reacted for 4 hours, followed by the addition of 100 µl of lysis buffer to stop the reaction. The plates were read on an ELISA reader at wavelength of 570 nm to determine the survival rates. The half inhibition concentration ($IC_{50}$) values were also calculated and listed in Table 4.

TABLE 4

Results from in vitro add-on therapy toward hepatic cancer cells

| Samples | Results |
|---|---|
| Control group | Cell survival rate (%) |
| Hep 3B (0.0043 µg/ml Lovastatin) | 61 ± 3 |
| Hep G2 (0.0017 µg/ml Taxol) | 81 ± 2 |
| Experiment group | $IC_{50}$ (µg/ml) |
| Hep 3B (0.0043 µg/ml Lovastatin + formula 2) | 0.002 |
| Hep G2 (0.0017 µg/ml Taxol + formula 2) | 0.008 |

From the result of table 4, the $IC_{50}$ values of 4-hydroxy-2,3-dimethoxy-6-methyl-5(3,7,11-trimethyl-dodeca-2,6,10-trienyl)-cyclohex-2-enone toward Hep 3B and Hep G2 dropped to 0.002 µg/ml and 0.008 µg/ml respectively with the added synergistic activities of Lovastatin and Taxol. Therefore these results confirm the inhibitory activity of 4-hydroxy-2,3-dimethoxy-6-methyl-5(3,7,11-trimethyl-dodeca-2,6,10-trienyl)-cyclohex-2-enone from Antrodia camphorata can be applied to inhibit the growth of hepatic cancer cells, and showed better antitumor synergistic activity for tumors when combined with Taxol.

Example 6

In Vitro Survival Assay for Anti-Prostate Cancer Effects

The NCI anti-cancer drug screen model was also adopted to test the anti-cancer effect of the compound isolated from example 1 in the present invention. The isolated compound of 4-hydroxy-2,3-dimethoxy-6-methyl-5(3,7,11-trimethyl-dodeca-2,6,10-trienyl)-cyclohex-2-enone from example 1 was added into the culture media of human prostate cancer cells, LNCaP or DU-145, for tumor cell survival assay.

The human hepatic-cancer cells, LNCaP and DU-145, were separately cultivated in media containing fetal calf serum for 24 hours. The proliferated cells were washed once with PBS, then treated with 1× trypsin-EDTA and centrifuged at 1200 rpm for 5 minutes. The supernatant was discarded and the cell pellet was resuspended in 10 ml of fresh culture medium by gently shaking. The cells were placed in a 96-well plate. Ethanol extracts of Antrodia camphorata (the control group, total extracts of Antrodia camphorata without purification) or 4-hydroxy-2,3-dimethoxy-6-methyl-5(3,7,11-trimethyl-dodeca-2,6,10-trienyl)-cyclohex-2-enone (the experiment group) were added into each of the 96 wells at the following concentrations: 30, 10, 3, 1, 0.3, 0.1 and 0.03 μg/ml, respectively. The cells were incubated at 37° C. in a 5% $CO_2$ incubator for 48 hours. MTT was added in a concentration of 2.5 mg/ml into each well in dark and incubated for 4 hours, followed by the addition of 100 μl of lysis buffer to stop the reaction. The plates were read on an ELISA reader at wavelength of 570 nm to determine the survival rates. The half inhibition concentration ($IC_{50}$) values were also calculated and listed in Table 5.

TABLE 5

Results of in vitro survival assay for inhibition of prostate cancer cells

| Samples | $IC_{50}$ (μg/ml) |
|---|---|
| Control group (total extracts of *Antrodia camphorata*) | |
| LNCaP | 11.491 |
| DU-145 | 41.392 |
| Experiment group (formula 2) | |
| LNCaP | 2.378 |
| DU-145 | 1.812 |

From the result of table 5,4-hydroxy-2,3-dimethoxy-6-methyl-5(3,7,11-trimethyl-dodeca-2,6,10-trienyl)-cyclohex-2-enone is a potent inhibitor of the growth of human hepatic cancer cell line. The $IC_{50}$ values of 4-hydroxy-2,3-dimethoxy-6-methyl-5(3,7,11-trimethyl-dodeca-2,6,10-trienyl)-cyclohex-2-enone toward LNCaP and DU-145 are 2.378 μg/ml and 1.812 μg/ml respectively, which are significantly lower than those of total extracts from Antrodia camphorata. Therefore 4-hydroxy-2,3-dimethoxy-6-methyl-5(3,7,11-trimethyl-dodeca-2,6,10-trienyl)-cyclohex-2-enone from Antrodia camphorata can be applied to inhibit the growth of prostate cancer cells.

Example 7

In Vitro Add-on Study Toward Adjuvant Therapy of Prostate Cancer Cells

The experiment was also carried out according to NCI anti-cancer drug screen in vitro model. The human prostate cancer cells, LNCaP and DU-145 were separately cultivated in media containing fetal calf serum for 24 hours. The proliferated cells were washed once with PBS, then treated with 1× trypsin-EDTA and centrifuged at 1200 rpm for 5 minutes. The supernatant was discarded and the cell pellet was resuspended in 10 ml of fresh culture medium by gently shaking. The LNCaP cells were treated with 0.0017 μg/ml of Taxol for 72 hours and DU-145 cells were treated with 0.0043 μg/ml of Taxol for 72 hours before placing in a 96-well plate. 4-hydroxy-2,3-dimethoxy-6-methyl-5(3,7,11-trimethyl-dodeca-2,6,10-trienyl)-cyclohex-2-enone obtained from example 1 were added respectively into each of the 96 wells at the following concentrations: 0 μg/ml (the control group); 30, 10, 3, 1, 0.3, 0.1 and 0.03 μg/ml (the experiment group). The cells were incubated at 37° C. in a 5% $CO_2$ incubator for 48 hours. MTT was added in a concentration of 2.5 mg/ml into each well in dark and reacted for 4 hours, followed by the addition of 100 μl of lysis buffer to stop the reaction. The plates were read on an ELISA reader at wavelength of 570 nm to determine the survival rates. The half inhibition concentration ($IC_{50}$) values were also calculated and listed in Table 6.

TABLE 6

Results from in vitro Taxol add-on therapy toward hepatic cancer cells

| Samples | Results |
|---|---|
| Control group | Cell survival rate (%) |
| Hep 3B (0.0017 μg/ml Taxol) | 56 ± 3 |
| Hep G2 (0.0043 μg/ml Taxol) | 70 ± 2 |
| Experiment group | $IC_{50}$ (μg/ml) |
| Hep 3B (0.0017 μg/ml Taxol + formula 2) | 0.961 |
| Hep G2 (0.0043 μg/ml Taxol + formula 2) | 0.515 |

From the result of table 6, the $IC_{50}$ values of 4-hydroxy-2,3-dimethoxy-6-methyl-5(3,7,11-trimethyl-dodeca-2,6,10-trienyl)-cyclohex-2-enone toward human prostate cancer cells MCF-7 and MDA-MB-231 decreased to 0.961 μg/ml and 0.515 μg/ml respectively after combined with Taxol. Therefore these results confirm the inhibitory activity of 4-hydroxy-2,3-dimethoxy-6-methyl-5(3,7,11-trimethyl-dodeca-2,6,10-trienyl)-cyclohex-2-enone from Antrodia camphorata can be applied to inhibit the growth of prostate cancer cells, and showed better antitumor synergistic activity for tumors when combined with Taxol.

Example 8

In Vitro Antioxidant Activity Study

Human low density lipoprotein (LDL) oxidated with copper ion ($Cu^{2+}$) has been widely employed to assess antioxidant activities of samples to be assayed. Antioxidant activity of a sample is determined by the diene contents of LDL after oxidation and expressed in Trolox equivalents by using a standard curve calculated from the water-soluble vitamin E analogue Trolox standards (the antioxidant capacity value of 1 is expressed in terms of 2 μM of Trolox).

The following solutions were prepared firstly: double distilled water (the negative control group), 5 mM sodium phosphate buffer (SPB), 1 μM and 2 μM Trolox solution (the positive control group), and 40 μg/ml 4-hydroxy-2,3-dimethoxy-6-methyl-5(3,7,11-trimethyl-dodeca-2,6,10-trienyl)-cyclohex-2-enone isolated from example 1. The concentration of LDL cholesterol (LDL-C) was determined using enzyme reaction method, which was diluted to 0.1-0.25 mg/ml with 5 mM SPB. One hundred μl of the LDL was added into each well of a 96-well quartz plate, followed by addition of the abovementioned Trolox and the isolated compound from example 1. Standardized oxidizing agent $CuSO_4$ was supplemented to induce oxidation at a final concentration of 5 μM in each 250 μl well. The plate was read on an ELISA reader at wavelength of 232 nm at 37□ for 12 hours. The sampling time was 15 min. The results were shown in Table 7.

TABLE 7

Results of in vitro antioxidant activity study

| Samples | Tlag(min) | ΔTlag(min) | Capacity values |
|---|---|---|---|
| negative control | | | |
| $H_2O$ ($Tlag_0$) | 185 | | |
| positive control | | | |
| 1 μM Trolox | 266 | 81 | 0.48 |
| 2 μM Trolox | 344 | 159 | 1.00 |
| experiment group | | | |
| 40 μg/mL formula 2 | 439 | 208 | 1.30 |

Note 1: The lag phase time (Tlag, min), was defined as the intersection of the lag phase with the propagation phase of absorbance at 234 nm. ΔTlag (min) was defined as the difference of time between Tlag and $Tlag_0$ for each sample.
Note 2: A compound is defined to have antioxidant ability when the antioxidant capacity value is larger than 0.5.

From the result of table 7, the antioxidant capacity value of 4-hydroxy-2,3-dimethoxy-6-methyl-5(3,7,11-trimethyl-dodeca-2,6,10-trienyl)-cyclohex-2-enone is 1.3, which is much higher than the standard value of 0.5. Therefore the compounds of the invention possess antioxidant activity, which can be used as supplements for health foods, diets and drinks, medical products and cosmetics and contribute great beneficial effects on human health through their abilities in preventing cardiovascular diseases or mutation of cells.

What is claimed is:

1. A compound having the formula (1):

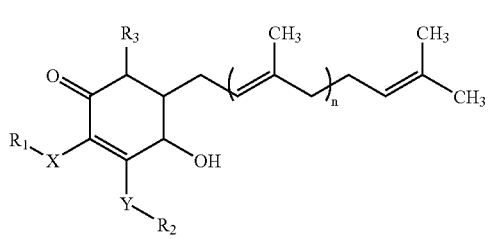

(1)

wherein X and Y are selected from oxygen or sulfur, $R_1$, $R_2$ and $R_3$ are each a hydrogen atom, methyl or $(CH_2)_m$—$CH_3$, and m=1-12, n=1-12.

2. The compound as claimed in claim 1, wherein the compound is isolated from Antrodia camphorata.

3. The compound as claimed in claim 2, wherein the compound is isolated from organic solvent extracts of Antrodia camphorata.

4. The compound as claimed in claim 3, wherein the organic solvents are selected from the group consisting of alcohols, esters, alkanes, and alkyl halides.

5. The compound as claimed in claim 4, wherein the alcohol is ethanol.

6. The compound as claimed in claim 2, wherein the compound is isolated from aqueous extracts of Antrodia camphorata.

7. The compound as claimed in claim 1, wherein the compound is 4-hydroxy-2,3-dimethoxy-6-methyl-5(3,7,11-trimethyl-dodeca-2,6,10-trienyl)-cyclohex-2-enone.

8. A method of inhibiting growth of breast cancer cells, comprising the application of a compound as claimed in claim 1 or claim 7.

9. The method as claimed in claim 8, wherein the compound is isolated from Antrodia camphorata.

10. The method as claimed in claim 9, wherein the compound is isolated from the organic solvent extracts of Antrodia camphorata.

11. The method as claimed in claim 10, wherein the organic solvents are selected from the group consisting of alcohols, esters, alkanes, and alkyl halides.

12. The method as claimed in claim 11, wherein the organic solvent is ethanol.

13. The method as claimed in claim 9, wherein the compound is isolated from the aqueous extracts of Antrodia camphorata.

14. The method as claimed in claim 8, wherein the breast cancer cells are from MCF-7 or MDA-MB-231 cell line.

15. A method of inhibiting growth of hepatic cancer cells, comprising the application of a compound as claimed in claim 1 or claim 7.

16. The method as claimed in claim 15, wherein the compound is isolated from Antrodia camphorata.

17. The method as claimed in claim 16, wherein the compound is isolated from the organic solvent extracts of Antrodia camphorata.

18. The method as claimed in claim 17, wherein the organic solvents are selected from the group consisting of alcohols, esters, alkanes, and alkyl halides.

19. The method as claimed in claim 18, wherein the organic solvent is ethanol.

20. The method as claimed in claim 16, wherein the compound is isolated from the aqueous extracts of Antrodia camphorata.

21. The method as claimed in claim 15, wherein the hepatic cancer cells are from Hep 3B or Hep G2 cell line.

22. A method of inhibiting growth of prostate cancer cells, comprising the application of a compound as claimed in claim 1 or claim 7.

23. The method as claimed in claim 22, wherein the compound is isolated from Antrodia camphorata.

24. The method as claimed in claim 23, wherein the compound is isolated from the organic solvent extracts of Antrodia camphorata.

25. The method as claimed in claim 24, wherein the organic solvents are selected from the group consisting of alcohols, esters, alkanes, and alkyl halides.

26. The method as claimed in claim 25, wherein the organic solvent is ethanol.

27. The method as claimed in claim 23, wherein the compound is isolated from the aqueous extracts of Antrodia camphorata.

28. The method as claimed in claim 22, wherein the prostate cancer cells are from LNCaP or DU145 cell line.

29. A compound as claimed in claim 1 or 7, which exhibits antioxidant activity.

30. A pharmaceutical composition for inhibiting growth of tumor cells comprising an active dose of the compound as claimed in claim 1 and a pharmaceutically-acceptable carrier, wherein the tumor cells are selected from the group consisting of breast cancer, hepatic cancer, and prostate cancer.

* * * * *

UNITED STATES PATENT AND TRADEMARK OFFICE
CERTIFICATE OF CORRECTION

PATENT NO. : 7,342,137 B1
APPLICATION NO. : 11/747407
DATED : March 11, 2008
INVENTOR(S) : Sheng-Yun Liu et al.

Page 1 of 1

It is certified that error appears in the above-identified patent and that said Letters Patent is hereby corrected as shown below:

Column 2, Formula (1) and Column 11, Formula (1) should be corrected to:

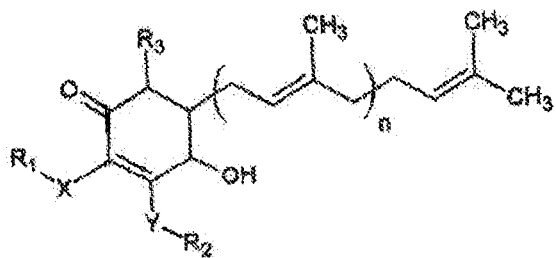

Signed and Sealed this
Fifth Day of April, 2011

David J. Kappos
Director of the United States Patent and Trademark Office